(12) United States Patent
Avilov et al.

(10) Patent No.: US 7,163,702 B1
(45) Date of Patent: Jan. 16, 2007

(54) PROCESS FOR ISOLATING SEA CUCUMBER SAPONIN FRONDOSIDE A, AND IMMUNOMODULATORY METHODS OF USE

(76) Inventors: Sergey Anatolievuch Avilov, Komsomolskay Street, 27-36, Vladivostok, 690014 (RU); Vladimir Ivanovich Kalinin, Prospect 100-Letiya Vladivostoka, 30v-16, Vladivostok, 690048 (RU); Alexandra Sergeevna Silchenko, Allilueva Street, 2a-118, Vladivostok, 690088 (RU); Dmitry Lvovich Aminin, 40-Let VLKSM Steet, 17-9, Vladivostok, 690016 (RU); Irina Grigorevna Agafonova, Kirova Street, 62-324, Vladivostok, 690068 (RU); Valentin Aronovich Stonik, Zavoika Street, 2-44, Vladivostok, 690048 (RU); Peter D. Collin, P.O. Box 172, Sunset, ME (US) 04683; Carl Woodward, 241 Burnt Cove Rd., Stonington, ME (US) 04681

( * ) Notice: Subject to any disclaimer, the term of this patent is extended or adjusted under 35 U.S.C. 154(b) by 0 days.

(21) Appl. No.: 11/145,580

(22) Filed: Jun. 6, 2005

Related U.S. Application Data

(60) Provisional application No. 60/579,355, filed on Jun. 14, 2004.

(51) Int. Cl.
*A61K 35/56* (2006.01)
*A61K 31/70* (2006.01)
*A61K 35/12* (2006.01)
*A01N 63/02* (2006.01)
*A61P 37/02* (2006.01)

(52) U.S. Cl. .............. 424/572; 424/520; 424/522; 424/537; 424/543; 424/548; 514/25; 514/26; 514/33; 514/34; 514/885

(58) Field of Classification Search ............... 424/520, 424/522, 537, 543, 548, 572; 514/25, 26, 514/33, 34, 885
See application file for complete search history.

(56) References Cited

U.S. PATENT DOCUMENTS

| | | | | |
|---|---|---|---|---|
| 4,428,876 | A | * | 1/1984 | Iwamura ............... 530/370 |
| 5,770,205 | A | | 6/1998 | Collin |
| 5,876,762 | A | | 3/1999 | Collin |
| 5,985,330 | A | | 11/1999 | Collin |
| 5,989,592 | A | | 11/1999 | Collin |
| 6,055,936 | A | * | 5/2000 | Collin ............... 119/215 |
| 6,541,519 | B1 | | 4/2003 | Collin et al. |
| 6,767,890 | B1 | | 7/2004 | Collin |

OTHER PUBLICATIONS

Findlay et al. Journal of Natural Products 1992, 55(1), 93-101.*
Silchenko et al. Can. J. Chem. 2005, 83, 21-27.*
Avilov et al. Can. J. Chem. 1998, 76, 137-141.*

* cited by examiner

*Primary Examiner*—Johann Richter
*Assistant Examiner*—Ernst V Arnold
(74) *Attorney, Agent, or Firm*—John D. Gugliotta

(57) ABSTRACT

This present invention discloses use of a chloroform/solvent mixture extraction at different solvent-to-feed ratios, followed by evaporation and extraction with ethyl acetate/water; followed by chromatography of the water phase in Teflon or other non-polar resin and Silica gel column chromatography for recovering of individual triterpene glycosides (saponins) of high purity from the freeze dried or spray dried cooking water or dried powderized tissues of the industrial processed sea cucumber *Cucumaria frondosa*. A resulting glycoside Frondoside A stimulates lysosomal activity of peritoneal macrophages, phagocytosis and oxidative burst in the macrophages at concentrations significantly less than for acute toxicity, hemolysis and sea urchin embryo toxicity.

4 Claims, 4 Drawing Sheets

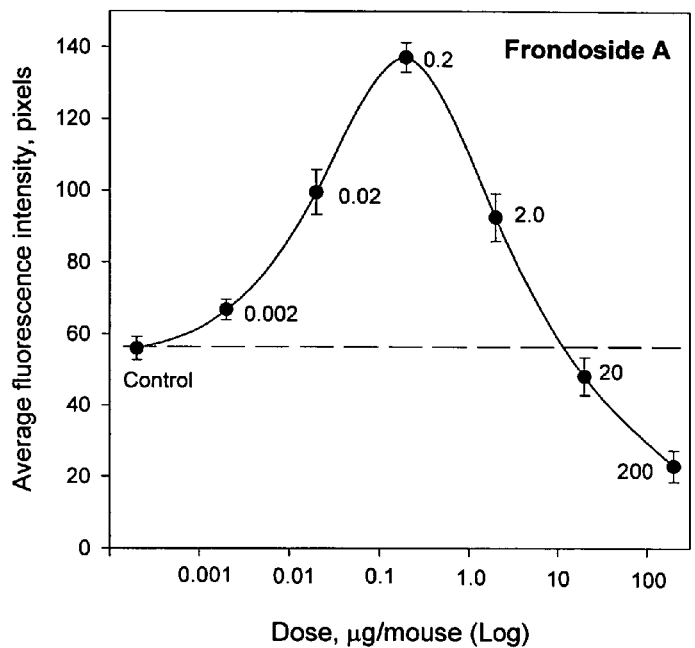

Fig. 1. Dose-response effect of Frondoside A upon lysosomal activity of BALB/c mouse peritoneal macrophages, application of. 0.5 ml of glycoside solution (in sterilized physiological solution, 0.9% NaCl $i.p.$) On the $4^{th}$ day after injection macrophages were isolated and lysosomal activity was quantified using acridine orange dye and fluorescent imaging system. Values are mean ±se (n=100); 3 mice (20g average weight) were used for each dose.

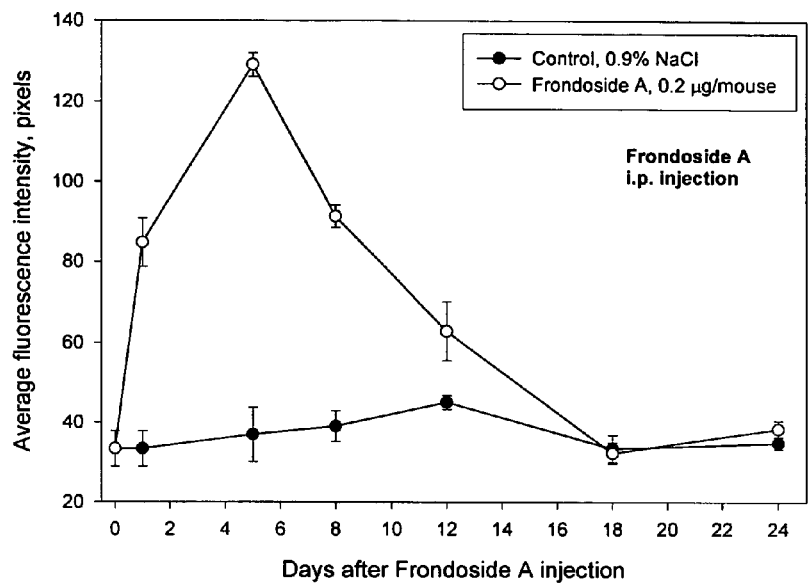

Fig. 2. Time-response effect of Frondoside A upon lysosomal activity of BALB/c mouse peritoneal macrophages, application of 0.5 ml of glycoside solution at dose of 0.2 µg/mouse (in sterilized physiological solution, 0.9% NaCl, *i.p.* ) On the certain days after injection macrophages were isolated and lysosomal activity was quantified using acridine orange dye and fluorescent imaging system. Values are mean ±se (n=100); 4 mice (20g overage weight) were used for each dose.

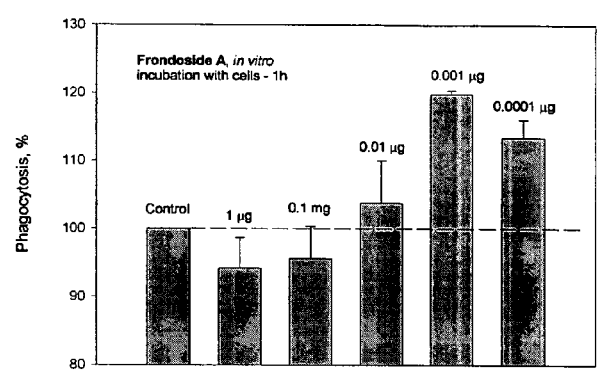
Fig. 3. *In vitro* effect of Frondoside A on mouse peritoneal macrophage phagocytosis of FITC-labelled *St. aureus*. Time of Frondoside A incubation with cells is 1 h.

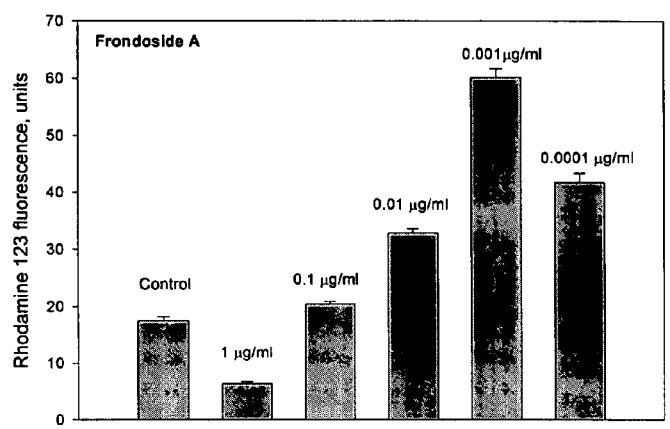
Fig. 4. Effect of Frondoside A applied at different concentration upon generation of reactive oxygen species (oxidative burst) in mouse peritoneal macrophages *in vitro*. Time of glycoside incubation with cells is 1 h. Values are mean ±se (n=100).

PROCESS FOR ISOLATING SEA CUCUMBER SAPONIN FRONDOSIDE A, AND IMMUNOMODULATORY METHODS OF USE

RELATED APPLICATIONS

The present invention claims the benefit of priority of U.S. Provisional Patent No. 60/579,355, filed on Jun. 14, 2004 and incorporated by reference as if fully rewritten herein.

BACKGROUND OF THE INVENTION

1. Field of the Invention

The present invention relates to saponins isolated from sea cucumbers, particularly the saponins known as Frondoside A.

2. Description of the Related Art

Saponins, or glycosides consisting of a sugar moiety and triterpene or steroid aglycon, are widely distributed in plants. Saponin distribution in animals is very limited. The presence of triterpene glycosides is characteristic for most sea cucumbers, the animals belonging to the class Holothurioidea (*phylum Echinodermata*) and for some sponges. Triterpene glycosides of the sea cucumbers have lanostane-type aglycons, most have aglycones with 18(20)-lactones and are referred to as holostane type. The carbohydrate moieties of the sea cucumber glycosides consist of two–six sugar residues, including xylose, quinovose, glucose, 3-O-methyl-glucose and (rarely) 3-O-methyl-xylose and may contain one, two or three sulfate groups. (V. A. Stonik, V. I. Kalinin, S. A. Avilov, "Toxins from Sea Cucumbers (*Holothuroids*): Chemical Structures, Properties, Taxonomic Distribution, Biosynthesis and Evolution," J. Nat. Toxins. 1999, 8, 235–248)

Because of the ability to form a complex with 5(6)-unsaturated sterols of cellular membranes, the glycosides possess a wide spectrum of biological activities including hemolytic, antifungal, cytotoxic, and many other kinds of membranotropic action. Moreover, these glycosides are known as having effective immunomodulatory action at very low concentrations that may have practical significance. (V. I. Kalinin, M. M. Anisimov, N. G. Prokofieva, S. A. Avilov, S. S. Afiyatullov, V. A. Stonik, "Biological activities and biological role of triterpene glycosides from holothuroids (*Echinodermata*)". Echinoderm Studies. Vol. 5, A. A. Balkema, Rotterdam, pp. 139–181, 1996) Immunomodulatory activity was studied for several species of holothurians. (D. L. Aminin, I. G. Agafonova, E. V. Berdyshev, E. G. Isachenko, S. A. Avilov, V. A. Stonik, "Immunomodulatory Properties of cucumariosides from the Edible Far-Eastern Holothurian *Cucumaria japonica*," J. Med. Food. 2001, 4, 127–135). It was shown that the most effective immunostimulants are monosulfated glycosides but di- and tri-sulfated are immunodepressants. The comlex of cholesterol and sum of monosulfated saponins from *C. japonica* (an ISCOM-like composition) and a composition thereof were used as immunostimulant also (V. A. Stonik, D. L. Aminin, V. M. Boguslavsky, S. A. Avilov, I. G. Agafonova, A. S. Silchenko, L. P. Ponomarenko, N. G. Prokofieva, E. A. Chaikina. Immunomodulatory preparation "Cumaside" and pharmacological composition there of" Russian Patent Application No. 2004120434/15, priority 02.07.2004).

Hence it is very significant to have a pure standard glycoside preparation in order to have a guaranteed and stable immunostimulant effect. Frondoside A, the subject of the present invention, differs significantly from other monosulfated glycosides such as the cucumarioside $A_2$-2 and other cucumariosides from *Cucumaria japonica* for which immunostimulatory properties were reported. (G. B. Elyakov, V. A. Stonik, "Marine bioorganic chemistry as the base of marine biotechnology", Rus. Chem. Bull. 2003, 52, 1–19 incorporated herein by reference). Therefore, the discovery of immunostimulation by Frondoside A of the present invention is novel and un-obvious because of the following points of differences between the cucumariosides and Frondoside A from *C. frondosa*:

1. Frondoside A has 16-OAc group at C-16 of the aglycon but not a keto group
2. Frondoside A has xylose as third monosaccharide residue but not glucose
3. Frondoside A does not have a double bond in the side chain of the aglycon.

Moreover, immunomodulatory action of Frondoside A is surprising and unexpected because cucumarioside $G_1$ which has very similar aglycone with the same 16-OAc group does not have immunomodulatory activity (Y. I. Grishin, N. N. Besednova, V. A. Stonik, S. A. Avilov, "Regulation of hemopoesis and immunogenesis by triterpene glycosides of the sea cucumbers" Radiobiologia, 1990, 30, 556)

*Cucumaria frondosa* is found in North Atlantic shallow waters and is harvested for food purposes in Maine and Canada. *Cucumaria frondosa* contains a very complicated mixture of mono-, di- and trisulfated glycosides, mainly pentaosides. (M. Girard, J. Belanger, J. W. ApSimon, F.-X. Garneau, C. Harvey, J.-R. Brisson, "Frondoside A. A Novel Triterpene Glycoside from the Holothurian *Cucumaria frondosa*," Can. J. Chem. 1990. 68, 11–18); (J. Findlay, N. Yayli, L. Radics, "Novel sulphated oligosaccharides from the sea cucumber *Cucumaria frondosa*," J. Nat. Prod. 1992, 55, 93–101); (Yayli, N., Findlay, J. "A Triterpenoid Saponin from *Cucumaria frondosa*," Phytochemistry. 1999, 50, 135–138); (N. Yayli, "Minor Saponins from the Sea Cucumber *Cucumaria frondosa*," Indian J. Chem. 2001, 40B, 399–404); (S. A. Avilov, O. A. Drozdova, V. I. Kalinin, A. I. Kalinovsky, V. A. Stonik, E. N. Gudimova, R. Riguera, C. Jimenez, "Frondoside C, a New Nonholostane Triterpene Glycoside from the Sea Cucumber *Cucumaria frondosa*: Structure and Cytotoxicity of its Desulphated Derivative", Can. J. Chem. 1998, 76, 137–141) During industrial processing of the sea cucumbers, significant amounts of cooking water containing saponins is formed as a waste product. However immunomodulatory properties of individual glycosides from *C. frondosa* were never studied.

Lysosomal activity is a one of the important markers of physiological and biochemical status of macrophages. The enhanced number of their intracellular organelles and their enlarged size, as well as increased acidity indicates activation of some cellular functions and lysosomal enzymes, and preparation of the cells for phagocytosis and digestion of absorbed particles. (A. C. Allison, M. R. Young. Vital Staining and Fluorescence Microscopy of Lysosomes. In "Lysosomes in Biology and Pathology". Vol. 2, North Holland, Amsterdam, pp. 600–628, 1969); (C. Millot, "Characterization of Acidic Vesicles in Multidrug-Resistant and Sensitive Cancer Cells by Acridine Orange Staining and Confocal Microspectrofluorometry", J. Histochem. Cytochem. 1997, 45, 1255–1259); (F. Zoccarato, L. Cavallini, A. Alexandre, "The pH-Sensitive Dye Acridine Orange as a Tool to Monitor Exocytosis/Endocytosis in Synaptosomes", J. Neurochem. 1999, 72, 625)

Phagocytosis is an important mechanism for nourishment in unicellular organisms and for host defense against infection in higher vertebrates. The process of phagocytosis can be observed and quantitated in human polynuclear cells and mouse macrophages by following the internalization of a foreign particle such as fluorescently labeled immune complexes and bacterial particles. This technique takes advantage of the detectability of the intracellular fluorescence emitted by the engulfed particles, as well as the effective fluorescence quenching of the extracellular probe by trypan blue. (C. R. Uff, A. G. Pockley, R. K. Phillips, "A Rapid Microplate-Based Fluorometric Assay for Phagocytosis." Immunol Invest. 1993, 22, 407); (C. P. Wan, C. S. Park, B. H. Lau, "A Rapid and Simple Microfluorometric Phagocytosis Assay." J Immunol Meth. 1993. 162, 1)

The ability to generate reactive oxygen species (ROS), the so-called oxidative burst, is also essential for macrophages to kill infectious microorganisms. Conversion of dihydrorhodamine 123 to rhodamine 123 in cells detected in the present study reflects a production of mouse macrophage $H_2O_2$, $O_2$ and peroxynitrite, which is associated with nitric oxide production and NADPH-oxidase dependent superoxide formation. These reactive oxygen species are very toxic and necessary for absorbed microorganisms killing, oxidation and disintegration. (E. W. Childs, K. F. Udobi, J. G. Wood, F. A. Hunter, D. M. Smalley, L. Y. Cheung, "In vivo Visualization of Reactive Oxidants and Leukocyte-Endothelial Adherence Following Hemorrhagic Shock," Shock. 2002. 18, 423–7); (S. F. Emmendorffer, M. Hecht, M.-L. Lohman-Mattes, J. Roester, "A Fast Easy Method to Determine the Production of Reactive Oxygene Intermediates by Human and Murine Phagocytes Using Dihydrorodamine 123," J. Immunol. Meth. 1990, 131, 269–275)

In comparison with terrestrial saponin-containing plants, isolation of saponins from the sea cucumbers is generally different in such aspects as: polar character of most of the glycosides; presence of more significant amounts of proteins, peptides, lipids and salts in the animals. The most common approach to the isolation of the glycosides is extraction of crude animal material with 70% ethanol or methanol, desalting of the evaporated extract on hydrophobic resin such as XAD-4 etc. and followed by chromatography on Silica gel followed by isolation of individual substances on HPLC. (S. A. Avilov, A. S. Antonov, A. S. Silchenko, V. I. Kalinin, A. I. Kalinovsky, P. S. Dmitrenok, V. A. Stonik, R. Riguera, C. Jimenez, "Triterpene Glycosides from the Far Eastern Sea Cucumber *Cucumaria conicospermium*," J. Nat. Prod. 2003, 66, 910–916); (H. D. Chludil, C. C. Muniain, A. M. Seldes, M. S. Maier, "Cytotoxic and Antifungal Triterpene Glycosides from the Patagonian Sea Cucumber *Hemoidema spectabilis*", J. Nat. Prod. 2002, 65, 860–865)

However, a similar procedure is not convenient for industrial or semi-industrial purposes because of colloid character of the water solution of dried ethanol or methanol extract containing a lot of particles of different non-polar compounds such as lipids, pigments etc. that may delay the solvent flow through Teflon or any other non-polar resin column. The isolation of the glycosides from cooking water by direct hydrophobic chromatography on Teflon or any other non-polar resin after filtration of the cooking water is difficult also because of irreversible adsorption of hydrophobic proteins that leads to gradual loss of the adsorption properties by corresponding column. The flow of the solvent is also delayed with colloid particles of different proteins. Moreover, a significant part of the glycosides may form a complex with hydrophobic proteins and be lost at filtration.

SUMMARY OF THE INVENTION

It is an object of the present invention to provide industrially relevant and effective means of isolating the sea cucumber glycoside, Frondoside A from sea cucumber food processing operations, or sea cucumber tissue, and especially the 'cooking water' by-product of such processing. An additional object of the present invention is to provide means of guaranteed stable stimulating and/or potentiating of the immune system of a mammal in need of same, and especially industrially farmed animals, or pet ferrets at risk of viral, fungal, or opportunistic diseases associated with decreased immunological response by the mammal.

It is an additional object of the present invention to provide an effective medicament for use by immunocompromised animals, especially humans, including, but not limited to humans infected with the HIV virus, and humans during disease treatment involving radiation or chemotherapy. Additionally, such medicament may be in any form appropriate as determined by any person skilled in the health-therapy arts.

Present invention is directed to a method for recovering Cucumaria frondosa saponins which comprises:

i) extracting (a) freeze dried form of water which had been used to cook *Cucumaria frondosa* in the industrial processing of *Cucumaria frondosa*, wherein said water contains *Cucumaria frondosa* residues, or (b) dried and powdered tissues of *Cucumaria frondosa* with a mixture of chloroform and methanol under reflux to obtain an organic extract;

ii) evaporating the extract;

iii) extracting the evaporated extract with ethyl acetate and water one or more times to obtain an aqueous phase;

iv) combining the aqueous phase from each ethyl acetate and water extraction;

v) performing chromatography of the aqueous phase on Teflon or other non-polar resin and Silica gel columns; and vi) collecting the eluate to obtain *Cucumaria frondosa* saponins.

DETAILED DESCRIPTION OF SPECIFIC EMBODIMENTS

Isolation Procedure

The present invention utilizes a chloroform/methanol solvent mixture of different proportional ratios to solid material followed by evaporation and extraction with ethyl acetate/water and followed by chromatography of the water phase with Teflon or other non-polar resin and Silica gel columns. This process is used for recovering triterpene glycosides (saponins) of high purity, especially Frondoside A from the dried cooking water of industrially processed sea cucumber *Cucumaria frondosa*. This method can also be used with other sea cucumber dried and powdered tissues instead of only dry cooking water residues. The present invention also discloses a method to stimulate macrophage lysosomal activity, phagocytosis and oxidative burst activity in a mammal by administration of Frondoside A.

Although polar saponins are not easily soluble in chloroform/methanol mixture without addition of water, the mixture of chloroform and methanol was surprisingly found to be capable of dissolving saponins at elevated temperatures under reflux. The temperature may be controlled by different amounts of the solvent because the higher the solvent to feed ratio, the less the boiling temperature of the extract achieved. Full extraction of the saponins including di- and trisulfated pentaosides with chloroform/methanol in approximate proportional ratio 1:1 is possible with the amount of the solvent in approximate proportional ratio of 4 mL of solvent system to 1 g of dried cooking water during 1.5 hours reflux or more. Accordingly, the higher the amount of the solvent, namely in approximate proportional ratio of 6 mL of solvent system to 1 g of dried cooking water was used, the more selective was the extraction of the monosulfated glycosides, mainly Frondoside A. However, the direct chromatography of evaporated and redissolved in water chloroform/methanol extract on Teflon or other non-polar resin, is not quite effective because of significant amounts of lipid material. Effective delipidization and elimination of pigments is achieved with the water/ethyl acetate extraction. The resulting water phase is almost totally free of pigments and lipids.

Further desalting with Teflon resin is realized by loading the water phase diluted with water about 8–10 times to the column; washing it with water until the elute is completely desalted and then eluting with acetone (or other water soluble polar organic solvent, such as methanol, ethanol, isopropanol etc.) or polar solvent/water mixture with a TLC control that allows the separation of the glycosides and the trace amounts of remaining lipids. The water phase ought to be evaporated to dryness after water/ethyl acetate extraction at application of other kinds of hydrophobic resins (except of Teflon) in order to eliminate ethyl acetate traces.

The further purification of the glycosides may be accomplished by common chromatography on common low performance Silica gel column or using the simplest flash Silica gel column for final purification of the fraction containing Frondoside A as a major component and for purification of the fractions containing mono-, di- and trisulfated glycosides. The purity of yielded Frondoside A, 3-O-metyl-β-D-glucopyranosyl-(1→3)-β-D-xylopyranosyl-(1→4)-[β-D-xylopyranosyl-(1→2)]-β-D-quinovopyranosyl-(1→2)-4-O-sodium sulfate-β-D-xylopyranosyl-3-O-holost-7(8)-en-3β-ol-16β-O-acetate may be checked by $^{13}C$ NMR and mass-spectrometry.

The extraction of animal materials with chloroform/methanol mixtures is usually used for lipid isolation, and to our knowledge has never before been used for direct extraction of polar saponins from animal material and has never before been used for isolation of glycosides from the sea cucumber cooking water or separation of different saponins from each other. It was surprisingly found by the inventors that there is considerable advantage in loading the water phase from ethyl acetate/water onto a column with hydrophobic resin without preliminary evaporation of the sample. This is possible only on Teflon resin but not on XAD and has heretofore not been reported.

Similarly, procedures as described above can be used to isolate orally bioavailable saponins from sea cucumber, particularly C. frondosa, wherein the isolation method may comprise extracting a dried industrial processed Cucumaria frondosa cooking water or dried and powdered tissues of Cucumaria frondosa with a mixture of chloroform and methanol under reflux to obtain an organic extract, evaporating the extract, extracting the evaporated extract with ethyl acetate and water one or more times to obtain an aqueous phase, combining aqueous phase from each ethyl acetate and water extraction, performing chromatography of the aqueous phase on Teflon or other non-polar resin and Silica gel columns, collecting fixed-volume fractions of the eluate after chromatography, and then assaying each fraction after evaporation and re-dissolving in water for oral bioavailability testing by administering oral doses of collected fractions to a test animal, monitoring metabolites, and comparing results to placebo fractions.

Of course, the methodology for isolating saponins having oral bioavailability is by example only, and such protocols may be modified and optimized by one skilled in the art, without limit, and are envisioned to fall within the subject matter, scope and spirit of the herein disclosed invention.

In Vivo Testing

It was subsequently found by the inventors that Frondoside A, isolated from C. frondosa, in the range of 0.002–2.0 μg/mouse, caused significant immunostimulatory effect upon peritoneal macrophages in a dose-dependent manner. The injection of low doses of Frondoside A resulted in an increase in the number and volume of lysosomes as well as their acidity in mouse peritoneal macrophages, as measured by acridine orange fluorescence at day 4 after the treatment. The maximal stimulatory effect was detected at concentration of Frondoside A of 0.2 μg/mouse and it was estimated as more than two-fold stimulation of their lysosomal activity. On the other hand, the much bigger doses of 20 μg/mouse and 200 μg/mouse caused the opposite effect expressed as significant lysosomal activity suppression compared to control level.

After injection of Frondoside A significant stimulation occurred even on the first day after injection. The maximal stimulating effect of Frondoside A is on $4-5^{th}$ days after glycoside injection. After this period the effect decreased slowly and reached the control level on the $12th–18^{th}$ day. Hence the stimulatory effect of Frondoside A after a single injection was observed within two weeks.

Phagocytosis

Frondoside A acts as immunomodulator in a dose-depended manner on phagocytosis of Staphylococcus aureus bacterial cells by mice peritoneal macrophages in vitro. In the concentration range of 0.01–0.0001 μg/ml, Frondoside A stimulated phagocytosis of bacteria with maximal effect of about 20% at concentration of 0.001 μg/ml. At concentration of 0.01 μg/ml, the glycoside significantly inhibited phagocytosis and at concentration of 0.1 μg/ml the non-significant phagocytosis reduction was observed.

Effect on Reactive Oxygen Species

Frondoside A caused dual effect upon reactive oxygen species (ROS) or "oxidative burst" formation in macrophages in vitro. This effect depended on applied glycoside concentration. At the Frondoside A concentration range of 0.0001–0.01 μg/ml, the increase of green intracellular fluorescence of formed rhodamine 123 was detected. The stimulatory effect with maximal efficiency at concentration of 0.001 μg/ml was determined. On the other hand, Frondoside A applied at cytotoxic concentration of 1.0 μg/ml significantly inhibited the ROS generation, and concentration of 0.1 μg/ml was practically ineffective compared to control level.

The data obtained for Frondoside A influence on ROS formation and phagocytosis process in macrophages reflects the strong similarity in these activities that showed that Frondoside A acts as a direct modulator of cellular immunity.

Toxicity

Acute toxicity of Frondoside A obtained on white mice was determined as 9.9 mg/kg. Hemolytic activity of Frondoside A against 1% suspension of mouse erythrocytes is 3.50 μg/ml ($EC_{50}$) or 12.50 μg/ml ($EC_{100}$). Sea urchin embryotoxicity of Frondoside A is 0.98 μg/ml ($EC_{50}$) or 3.12 μg/ml ($EC_{100}$).

These data show that imunostimulatory doses of Frondoside A are about two fold of magnitude less than toxic doses both in vivo and in vitro biotesting.

The stimulation of immune system of mammalian by administration of Frondoside A in subtoxic low concentrations has never before been reported.

Immunopotentiation Description and Diseases Associated with Decreased Immunocompetence The principal protective function of the immune system relates to resistance to invasion by pathogens, including viruses, *rickettsia*, mycoplasma, bacteria, fungi and parasites of all types. Thus, improvement of immune response, particularly when depressed, improves resistance to infection or infestation by any of the above pathogens.

A second protective function of the immune system is to resist engraftment of foreign tissue, either natural or in fetal-maternal relationship; or unnatural as in organ transplant procedures.

A third protective function involves maintaining non-reactivity to self by positive suppressor mechanisms. In auto-immune and related disorders, immune reactivity is directed at self antigens or exaggerated, elevated, destructive immune responses are apparent.

Generally the immune system includes such functional components as cellular immunity system and humoral immunity. The immunity may be specific or nonspecific, inherent etc. The basic aim of immunotherapy is the correction of different immunodeficiency conditions. Immunomodulators normalize the functioning of some or/and all parts of immune system of animals and humans with inherent or acquired immunodeficiency. It has now been found that Frondoside A or physiologically acceptable compositions thereof, acts as an immunopotentiator and influences cellular immunity of the organism.

Therefore, the compound of the invention or physiologically acceptable compositions thereof may be used for the treatment of diseases where there is a defect in the immune system and/or an ineffective host defense mechanism, or to enhance activity of the immune system above normal levels.

The present invention provides for the use of Frondoside A or physiologically acceptable compositions there of for the manufacture of a medicament for the potentiation of an immune response.

The pharmaceutical composition may be a tablet form includes Frondoside A as an active compound and additionally potato amylum and gypsum as a filling material in following ratio on 1 tablet, mg: Frondoside A—0.05; potato amylum—45.0; gypsum—5.0. or Frondoside A—0,05; sorbitum—45,0; calcium stearate—5,0.

The physiological composition of Frondopside A may be an ISCOM as is generally known by those skilled in the immunostimulation arts. The immunostimulating complex (ISCOM) is a vaccine formulation which combines a multimeric presentation of antigen with a built-in adjuvant [Hoglund, S., Dalsgaard, K., Lovgren, K., Sundquist, B., Osterhaus, A. and B. Morein. "Iscoms and immunostimulation with viral antigens." In: Subcellular biochemistry (Ed. Harris, J. R.) Plenum, N.Y., 1989, pp. 39–68; Morein, B., Akerblom L. "The iscom—an approach to subunit vaccines." In: Recombinant DNA vaccines. Rationale and strategy (Ed. Isaacson, R. E.) Marcel Dekker, New York, 1992, pp. 369–386; Morein B., Villacres-Eriksson M., Akerblom L., Ronnberg B., Lovgren K., Sjolander A. 1994. "Mechanisms behind the immune response induced by immuno-stimulating complexes." Aids Research and Human Retroviruses 10(S2): S109–S114; Morein B., Lovgren K., Ronnberg B., Sjolander A. and Villacres-Eriksson M. 1995. "Immunostimulating complexes: Clinical potential in vaccine development." Clinical Immunotherapeutics 3: 461–475.]. ISCOM's have a cage-like structure composed of saponins, cholesterol, phospholipids, and protein. Typically, ISCOMs have icosahedral symmetry, are 30–40 nm in diameter, and are composed of 12-nm ring-like subunits. ISCOM-borne antigen induces an enhanced, cell-mediated immune response, delayed-type hypersensitivity reaction, and cytotoxic T lymphocyte response under MHC class I restriction. Increased expression of MHC class II molecules has also been reported in primary as well as in recall immunization with ISCOMs. Experimental ISCOM vaccine formulations have induced protective immunity to a number of microorganisms encompassing viruses including retroviruses, parasites and bacteria in several species, including primates. Use of ISCOMs as an oral or intranasal immunization vector for vaccination with natural or recombinant antigens represents a new direction in antigen delivery that could increase elicited protective immune response, and may also have potential marketability in vaccine development for future use in the animal health industry. ISCOMs are stable particles made up of saponins and lipids arranged into multimolecular structures that contain entrapped antigens or not, and have been shown in bacterial and viral models to give enhanced immune responses by various delivery routes at both the humoral and cellular level. These unique abilities make ISCOMs excellent candidates for use in the poultry industry with parasite, viral and bacterial vaccines.

ISCOMs represent an interesting approach to stimulation of the humoral and cell-mediated immune response towards amphipathic antigens. It is a relatively stable but non-covalently-bound complex of a saponin adjuvant, cholesterol and amphipathic antigen. The spectrum of viral capsid antigens and non-viral amphipathic antigens of relevance for human vaccination, incorporated into ISCOMs, comprises influenza, measles, rabies, gp340 from EB-virus, gp120 from HIV, *Plasmodium falciparum* and *Trypanosoma cruzi*. The procedure for preparation of ISCOMs comprises solubilization of amphipathic proteins in preferably nonionic detergents, addition of a glycoside, cholesterol, and phosphatidylcholine. In the presence of amphipathic proteins, ISCOM particles are formed on removal of the detergent. If no protein (antigen) is present in the mixture, ISCOM MATRIX is formed. The unique components of an example of an ISCOM MATRIX is a sea cucumber glycoside exhibiting a unique affinity to cholesterol facilitating the stability of the complex.

Despite their complexity, sea cucumber ISCOMs are relatively easy to make by those skilled in the arts. Ideally, ingredients are used in a molar ratio of 1:1:1:1 of glycoside such as Frondoside A or other holothurian glycoside, cholesterol, phosphotidylcholine and antigen, or no antigen. In the centrifugation method, the latter 3 components, including antigen are placed on top of a 10–40% sucrose gradient containing 0.1% ISCOM-grade glycoside and a neutral, low ionic strength buffer. The tube is ultra-centrifuged for 4 hours at 150000 g, and ISCOMs form at 19S near the middle of the gradient. These are subsequently washed by re-centrifugation through 20% sucrose. If detergents with high critical micelle concentrations are used for antigen preparation (eg. when isolating viral envelope proteins), then the dialysis method for ISCOM preparation is recommended. In this procedure, the 3 reaction components are mixed with ISCOM-grade glycoside to give a final glycoside concentration of 0.1%. Following 24 hour dialysis to remove the detergent, ISCOMs will form and excess glycoside is removed by 20% sucrose ultra-centrifugation. ISCOMs can be administered orally, intranasally or subcutaneously. Optimal doses can be determined the first time ISCOMs are used with a given antigen.

There are a variety of circumstances in which the immune system may be defective or deficient. Thus, for example immune system deficiency is common in immature or premature infants (neonates). It may also result from suppression by certain drugs, which may be deliberate e.g. as a side-effect or cancer chemotherapy. Disordered growth of one or more constituent parts of the immune system, e.g. as in certain forms of cancer, may also result in immunodeficiency. Immune deficiency may furthermore be caused by viral infections, including human immunodeficiency virus (HIV). Farm raised swine, pets and other food animals can have depressed immunological functions due to population densities and communicable pathogens.

A further aspect of the present invention provides a method of treating immunodeficient patients or mammals, which comprises administering to a mammal (including human) an effective amount of Frondoside A, or a physiologically acceptable composition thereof including any ISCOM or any ISCOM-like compositions (without antigen). By an "effective amount" is meant the amount of Frondoside A which will restore or increase immune function to or near normal levels, or increase immune function above normal levels in order to eliminate infection, bacterial or viral pathology. Administration of specific dosages of such immunomodulators may be determined ultimately by persons skilled in the arts, based upon data supplied herein.

Frondoside A or physiologically acceptable compositions may be administered for the treatment or prophylaxis of immunodeficient mammals alone or in combination with other therapeutic agents, for example, with other antiviral agents, or with other anticancer agents.

A further aspect of the present invention provides for the use of Frondoside A or physiologically acceptable composition thereof including any ISCOM or any ISCOM-like compositions (without antigen) for the treatment and/or prophylaxis of acute and chronic viral infections.

Examples of acute viral infections against which immunopotentiatory therapy with Frondoside A or physiologically acceptable composition thereof including any ISCOM or any ISCOM-like compositions (without antigen) may be used, preferably in conjunction with an antiviral agent, are:

Herpes viruses, influenza viruses, parainfluenza viruses, adenoviruses, coxsakie viruses, picorna viruses, rotaviruses, heptatis A virus, mumps virus, Aleutian Disease virus affecting mink and ferrets, rubella virus, measles virus, pox viruses, respiratory syncytial viruses, papilloma viruses, and enteroviruses, arenavirus, rhinoviruses, poliovirus, Newcastle disease virus, rabies virus, arboviruses, and generally, viral pathogens common to industrially raised farm animals.

Examples of chronic viral infections against which immunopotentiatory therapy with Frondoside A or physiologically acceptable compositions thereof including any ISCOM or any ISCOM-like compositions (without antigen) may be used are: persistent herpes virus infections, Epstein Barr virus infection, persistent rubella infections, papovirus infections, hepatitis virus infections and human immunodeficiency virus infection.

The present invention is applicable to the treatment of viral hepatitis in all of its forms, five types now being recognized; hepatitis A, B, C, D and E respectively.

Of the DNA viruses, those of the herpes group are the sources of the most common viral illnesses in man. The group includes herpes simplex virus (HSV), varicella zoster virus (VZV), cytomegalovirus (CMV); Epstein-Barr virus (EBV) and human herpes virus 6 (HHV6). HSV 1 and HSV 2 are some of the most common infectious agents of man. Most of these viruses are able to persist in the host's neural cells; once infected, individuals are at risk of recurrent clinical manifestations of infection which can be both physically and psychologically distressing.

Of the RNA viruses, one group has assumed a particular importance; this is the retroviruses. Retroviruses form a sub-group of RNA viruses which, in order to replicate, must first reverse transcribe the RNA of their genome into DNA ("transcription" conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell. In the case of immunosuppression resulting from HIV infection, prophylaxis may be required by those diagnosed as seropositive for HIV i.e. having antibodies to HIV, and those with PGL (progressive generalised lymphadenopathy) or ARC (AIDS-related complex) as well as patients suffering from AIDS or patients suffering from AIDS-like immune deficiencies where the HIV infection is not detectable and who also require immunorestoration by means that are not specific to any particular virus.

The compounds according to the invention may be employed alone or in combination with other therapeutic agents for the treatment of the above infections or conditions. Combination therapies according to the present invention comprise, the administration of at least one Frondoside A or a physiologically functional derivative thereof including any ISCOM or any ISCOM-like compositions (without antigen) and at least one other pharmaceutically active ingredient. The active ingredient(s) and pharmacologically active agents may be administered together or separately and, when administered separately this may occur simultaneously or sequentially in any order. The amounts of the active ingredient(s) and pharmacologically active agent(s) and the relative timings of administration will be selected in order to achieve the desired combined therapeutic effect. Preferably the combination therapy involves the administration of one Frondoside A or a physiologically functional derivative thereof including any ISCOM or any ISCOM-like compositions (without antigen) and one of the corresponding agents.

It has been reported (W. T. Hughes, "Treatment and Prophylaxis of *Pneumocystis carinii* pneumonia," Parasitology Today. 1987, 3, 332–335) that at least 60% of patients with acquired immunodeficiency syndrome (AIDS) suffer from *Pneumocystis carinii* pneumonia Without treatment, *Pneumocystis carinii* pneumonia is almost always fatal in immunocompromised hosts. The most widely used treatments for this condition are trimethoprim-sulphamethoxazole (cotrimoxaole) and pentamidine. However, both of these treatments have been reported to be only around 50–70% effective in AIDS patients and to produce a much higher than usual incidence of adverse reactions (about 50%) Trimethoprim-sulfamethoxazole or pentamidine for *Pneumocystis carinii* pneumonia in the acquired immunodeficiency syndrome. A prospective randomized trial., (C. B. Wofsy, Antimicrobial Agents Annual. 1986, 1, 377–400)

There is thus a need for new agents, especially for the prophylaxis of *P. carinii* pneumonia.

In another aspect the present invention provides the use of Frondoside A and physiologically acceptable compositions thereof including any ISCOM or any ISCOM-like compositions (without antigen) for the manufacture of a medicament for the treatment and/or prophylaxis of *Pneumocystis carinii* infections in mammals (including humans).

In a yet further aspect the present invention provides for the use of Frondoside A and physiologically acceptable composition thereof including any ISCOM or any ISCOM-like compositions (without antigen) to treat conditions resulting from relative or absolute T-cell deficiencies such as DiGeorge Syndrome, fungal infections, mycoplasma infections, tuberculosis, leprosy, and systemic lupus erythemotosus.

A further aspect of the present invention provides for the use, as a vaccine adjuvant, of Frondoside A or physiologically acceptable compositions thereof including any ISCOM or any ISCOM-like compositions (without antigen). A vaccine may therefore be prepared by formulating the antigenic component with Frondoside A.

Frondoside A may be administered to the mammalian recipient by a route selected from oral, parenteral (including subcutaneous, intradermal, intramuscular and intravenous), rectal and inhalation. The size of an effective dose of a compound will depend upon a number of factors including the identity of the recipient, the type of immunodepletion involved, the severity of the condition to be treated and the route of administration, and will ultimately be at the discretion of the attendant physician.

For each of the aforementioned conditions, such an effective dose will generally be in the range 1 to 20 μg/kg bodyweight of human or mammalian recipient per day, preferably in the range 1 to 15 μg/kg bodyweight per day and most preferably in the range 8 to 11 μg/kg bodyweight per day; an optimum dose is 10 μg/kg bodyweight per day. The above doses are for a human usage, optimally re-administered every 10 days for maximal immune system stimulating effect.

While it is possible for Frondoside A to be administered as the raw chemical it is preferable to present them as a pharmaceutical formulation preparation. The formulations of the present invention comprise a Frondoside A, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, parenteral, intra-pulmonary (including subcutaneous, intradermal, intramuscular) and rectal administration although the most suitable route may depend upon for example the condition of the recipient. The formulations may conveniently be presented in unit dosage form and may be prepared by any of the methods well known in the art of pharmacy. All methods include the step of bringing into association Frondoside A (the active ingredient) with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion, an aerosol or a water-in-oil liquid emulsion. The active ingredient may also be presented as a bolus, electuary or paste.

A tablet may be made by compression, or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter.

Formulations suitable for pulmonary administration via the buccal cavity are presented such that particles containing the active ingredient and desirably having a diameter in the range 0.5 to 7 microns are delivered into the bronchial tree of the recipient.

As one possibility, such formulations are in the form of finely comminuted powders which may conveniently be presented either in a pierceable capsule, suitably of for example gelatin, for use in an inhalation device, or alternatively as a self-propelling formulation comprising active ingredient, a suitable liquid propellant and optionally other ingredients such as surfactant and/or a solid diluent. Self-propelling formulations may also be employed wherein the active ingredient is dispensed in the form of droplets of a solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example 50 to 100 microliters, upon each operation thereof.

As a further possibility, the active ingredient may be in the form of a solution for use in an atomizer or nebulizer whereby an accelerated airstream or ultrasonic agitation is employed to produce a fine droplet mist for inhalation.

Formulations suitable for nasal administration include presentations generally similar to those described above for pulmonary administration. When dispensed, such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution.

Preferred unit dosage formulations are those containing an effective dose, as hereinabove recited, or an appropriate fraction thereof, of the active ingredient.

Preferred unit dosage formulations are those containing a daily dose or unit daily subdose, as hereinabove recited, of a Frondoside A or physiologically acceptable composition thereof including any ISCOM or any ISCOM-like compositions (without antigen).

It should be understood that in addition to the ingredients particularly mentioned above the formulations of this invention may include other agents conventional in the art having regard to the type of formulation in question, for example those suitable for oral administration may include flavouring agents.

Frondoside A or physiologically acceptable compositions thereof including any ISCOM or any ISCOM-like compositions (without antigen) may also be presented as depot formulations of the kind known in the art from which the active ingredient is released, over a prolonged period, once the formulations is in place within the body of the recipient.

Frondoside A can be used as a means for animal treatment in case of immunodeficiency conditions in the event of viral or bacterial infections. Additionally, the invention provides a means of prophylaxis and treatment of Aleutian disease, cub diarrhea and other diseases accompanying by decrease of immunity of minks and ferrets. Also the preparations can be applied for increasing the number of new born animals and decreasing their death in early postnatal stage of development, inasmuch as immunocompetence is necessary for successful development and health in new born animals.

Cultivation of fur animals on the farms under artificial conditions requires highly effective veterinary preparations. Particularly, the chemical compound Frondoside A with the wide spectrum of physiological action can be taken as one such veterinary preparation. The typical cases of mass application are: before the rut, the presence of weakened immune systems, and diarrhea cubs, for the preventive maintenance and therapy of Aleutian disease. The wide spectrum of action and efficiency at low doses of Frondoside A, provide potential application in fur animal farming, or for companion animals in a home setting.

Farm raised swine, during the months after weaning, have increased mortality due to opportunistic infections by virus, bacteria and protozoa. Blecha et al. (J. Anim. Sci. 1983, 56, 396–400) and Wilcock and Schwartz (Salmonellosis, In: Diseases of Swine, 7th edition, Leman et al. (eds.), Iowa State University Press, Ames, Iowa, 1992, pp. 570–583) have disclosed that weaned pigs have an increased susceptibility to infectious diseases in comparison to mature and suckling swine. This increase in susceptibility to infectious agents post-weaning may be comprised of multiple factors, including loss of maternally derived antibodies, developmental deficiencies of the immune response, and stress-induced susceptibility due to increased glucocorticoids in these pigs [Blecha et al. (ibid); Wilcock and Schwartz (ibid); Blecha et al. (Am. J. Vet. Res. 1985, 46, 1934–1937); Aurich et al. (J. Reprod. Fert. 1990, 89, 605–612); Abughali et al. (Blood. 1994, 83, 1086–1092); and El-Awar and Hahn (J. Leuk. Biol. 1991, 49, 227–235].

With the trend leaning towards weaning piglets from sows earlier, 8–10 days of age in some cases, the influence of developmental deficiencies of the immune system on increased susceptibility to infectious diseases becomes an even more important concern (Blecha et al., ibid). Developmental deficiencies in immune functions and subsequent susceptibility to infectious diseases have been well documented in neonatal mammalian species. Human, equine and bovine neonates exhibit deficient or impaired neutrophil and T cell functions for the first weeks of life [Coignal et al. (Am. J. Vet. Res. 1984, 45, 898–901); Hauser et al. (Am. J. Vet. Res. 1986, 47, 152–153); Hill (Pediatric Research. 1997, 22, 375–382); Miller (Pediatrics. 1979, (suppl.), 709–712); Rosenthal and Cairo (Intern. J. Ped. Hem./One. 1995, 2, 477–487); Higuchi et al. (J. Vet. Med. Sci. 1997, 59, 271–276); Lee and Roth (Comp. Haem. Intern. 1992, 2,140–147); Lee and Kehrli (Am. J. Vet. Res. 1998, 59, 37–43); and Zwahlen et al. (J. Leuk. Biol. 1992, 51, 264–269)]. Susceptibility to gram negative bacteria has also been well documented in equine, porcine, and bovine neonates [Carter and Martens (Comp. Cont. Educ. Pract. Vet. 1986, 8, 256–270); Drieson et al. (Aust. Vet. J. 1993, 70, 259–262); and Selim et al. (Vaccine. 1995, 13, 381–390)]. Young pigs exhibit developmental deficiencies within both the humoral and cellular arms of the immune system. Development of B and T cell compartments in neonatal pigs takes several weeks to become stable and the different classes of immunoglobulins in various sites change with the age of the pig [Bianchi et al. (Vet. Immun. Immunopath. 1992, 33, 201–222) and McCauley and Hartmann (Res. Vet. Sci. 1984, 37, 234–241)]. Decreased mitogenic responses of T cells and decreased neutrophil function from young pigs have also been observed [Blecha et al. (1983, ibid); El-Awar and Hahn (ibid); Shi et al. (J. Leuk. Biol. 1994, 56, 88–94); and Hoskinson et al. (J. Anim. Sci. 1990, 68, 2471–2478)].

The method and immune stimulating compositions of this invention are effective for protecting swine and/or mink or ferrets against infection by a wide variety of microorganisms. Without being limited thereto, the process and compositions are useful for providing protection against viral, bacterial, fungal, and protozoan swine and ferret or mink pathogens, including those described in Wilcock and Schwartz (ibid) and The 1984 Yearbook of Agriculture: Animal Health [Hayes (ed.), U.S. Government Printing Office, LC 84-601135, 1984-451-784, pp. 277–306], the contents of each of which are incorporated by reference herein. In a preferred embodiment, the method and compositions are particularly effective for protecting swine against infection by *Salmonella* species such as *S. choleraesuis* and *S. typhimurium*. The invention may be practiced with any type of animal, including but not limited to ferrets, mink, pigs and hogs.

The results of tests with Frondoside A are described in the following Experimental examples in order to illustrate the effect of the present invention in more detail.

EXAMPLE 1

100 g of powdered freeze dried cooking water obtained from industrial *C. frondosa* food processing was loaded into 1-L flask and mixture of chloroform/methanol (C/M) added (1:1) (400 mL) and refluxed at warm water bath with careful heating, in order to avoid rapid boiling during 1.5 hr. The extract was then cooled and filtered through cotton wool using a common funnel. To the residue was then added a mixture of chloroform/methanol (1:1) (200 ml) and the liquid phase was decanted and filtered. These extracts were then combined and evaporated with control of excessive foaming by addition of a small amount of butanol.

The C/M evaporated extract was then dissolved in water in several steps by adding the water incrementally. The portion was decanted into a separate flask. As a result, about 0.7 L of colloid solution was obtained. 300 ml of ethyl acetate was then added to the solution. This mixture was then shaken for 3 hr by a magnet mixer and left to stand overnight for phase separation. The water phase was then decanted through a siphon hose. This stage may be kept for future processing. The water phase was then diluted with water 10 times and loaded on a Teflon Dupont No. 9B column (the size of Teflon column is about 1.5 L).

The Teflon column was then washed with water to remove salts and traces of pigments. The glycosides were then eluted with 65% acetone. The volume of each fraction was about 50 mL. Glycoside-containing fractions were then evaporated with butanol added as anti-foaming agent, and the column was then regenerated with pure acetone in amount of 2 column volumes. 850 milligrams of a crude glycoside mixture was obtained.

A Biotage Si 40 L 2632-2 flash column with the mobile phase mixture of chloroform/ethanol/water (100:100:17) as a solvent system was used. The sample of crude glycoside fraction after Teflon chromatography was dissolved in a minimal volume by adding the solvent mixture and water by drops and loaded to the column. The column was then eluted with about 0.5 L of this solvent mixture, collecting 10 ml fractions. After completing of Frondoside A elution, the solvent mixture was then changed to chloroform/ethanol/water (100:150:50). All the stages were controlled with TLC. The TLC solvent system was 100:100:17 cholorform/ethanol/water. 50 mg of Frondoside A, 136 mg of fraction of disulfated and 171 mg of trisulfated glycosides were obtained.

EXAMPLE 2

100 g of powdered freeze dried C. frondosa cooking water was loaded into 1-L flask and mixture of chloroform/methanol (C/M) added (1:1) (600 mL) and refluxed at a warm water bath with careful heating during 1.5 hr. The extract was then cooled and filtered through cotton wool using common funnel. To the residue was then added a mixture of chloroform/methanol (1:1) and the liquid phase was decanted and filtered. These extracts were then combined and evaporated with control of excessive foaming by addition of a small portion of butanol.

The C/M evaporated extract was then dissolved in water in several steps by adding the water incrementally. The portion was decanted into separate flask. As a result about 0.7 L of colloid solution was obtained. 300 mL of ethyl acetate was then added to the solution. This mixture was then shaken for 3 hr by magnet mixer and left to stand overnight for phase separation. The water phase was then decanted through a siphon hose. The water phase was then diluted with water 10 times and loaded on a Teflon Dupont No. 9B column (the size of Teflon column is about 1.5 L).

The Teflon column was then washed with water to remove salts and traces of pigments. Then the glycosides were eluted with 65% acetone. The volume of each fraction was about 50 mL. Glycoside containing fractions were then evaporated with butanol added as anti-foaming agent, and the column was then regenerated with pure acetone in amount of 2 column volumes. 110 mg of crude glycoside mixture containing Frondoside A as a major component was obtained.

A Biotage Si 40 L 2632-2 flash column with chloroform/ethanol/water (100:100:17) as a solvent system was next used. The sample of crude Frondoside A after Teflon chromatography was dissolved in a minimal volume by adding the solvent mixture and water by drops in a heated water bath and loaded to the column. The column was then eluted with about 0.5 L of this solvent mixture, collecting 10 ml fractions. All the stages were controlled with TLC. 50 mg of Frondoside A were obtained.

EXAMPLE 3

100 g of powdered freeze dried skin of C. frondosa was loaded into 1-L flask and mixture of chloroform/methanol (C/M) added (1:1) (400 mL) and refluxed at warm water bath with careful heating, in order to avoid rapid boiling during 1.5 hr. The extract was then cooled and filtered through cotton wool using a common funnel. To the residue was then added a mixture of chloroform/methanol (1:1) (200 ml) and the liquid phase was decanted and filtered. These extracts were then combined and evaporated with control of excessive foaming by addition of a small amount of butanol.

The C/M evaporated extract was then dissolved in water in several steps by adding the water incrementally. The portion was decanted into a separate flask. As a result, about 0.7 L of colloid solution was obtained. 300 ml of ethyl acetate was then added to the solution. This mixture was then shaken for 3 hr by a magnet mixer and left to stand overnight for phase separation. The water phase was then decanted through a siphon hose. This stage may be kept for future processing. The water phase was then diluted with water 10 times and loaded on a Teflon Dupont No. 9B column (the size of Teflon column is about 1.5 L).

The Teflon column was then washed with water to remove salts and traces of pigments. The glycosides were then eluted with 65% acetone. The volume of each fraction was about 50 mL. Glycoside-containing fractions were then evaporated with butanol added as anti-foaming agent, and the column was then regenerated with pure acetone in amount of 2 column volumes. 970 milligrams of a crude glycoside mixture was obtained.

A Biotage Si 40 L 2632-2 flash column with the mobile phase mixture of chloroform/ethanol/water (100:100:17) as a solvent system was used. The sample of crude glycoside fraction after Teflon chromatography was dissolved in a minimal volume by adding the solvent mixture and water by drops and loaded to the column. The column was then eluted with about 0.5 L of this solvent mixture, collecting 10 ml fractions. After completing of Frondoside A elution, the solvent mixture was then changed to chloroform/ethanol/water (100:150:50). All the stages were controlled with TLC. The TLC solvent system was 100:100:17 cholorform/ethanol/water. 65 mg of Frondoside A, 60 mg of fraction of disulfated and 246 mg of trisulfated glycosides were obtained.

EXAMPLE 4

BALB/c mice were used for an in vivo assay. The Frondoside A was injected intraperitoneally (0.5 mL of Frondoside A solution in distilled water). Distilled water was injected in control mice. Four days after treatment, the mice were killed by perivisceral dislocation and peritoneal macrophages were isolated using standard procedure.

An estimation of intracellular lysosome activity was conducted by staining and the localization of lysosomes in live macrophages with a fluorescent dye acridine orange followed by fluorescence image analysis. For this purpose, 250 µL of a BALB/c mice peritoneal fluid was applied on a microscope cover glass and left at 37° C. in an incubator for one hour. After adhesion of macrophages, the cover glasses were washed (3x) with phosphate-buffered saline (PBS, pH 7.5). 250 µL of acridine orange solution ("Calbiochem", 100 µg/ml in PBS) was added dropwise to the cell monolayer and glasses were incubated at 37° C. for 30 min. The cell monolayers were then washed (3×) in PBS. Cover glasses were mounted on a cell chamber of fluorescent imaging system based on inverted microscope Axiovert 200 (Zeiss, Germany). The 75 W Optosource xenon arc lamp and DAC-controlled Optoscan monochromator (Cairn Research Ltd., UK) was used as a light source to excite fluorescence at $\lambda$=489 nm; HQ FITC filter-block (Chroma Technology Corp., USA) and Fluar 40×/1.30 Oil objective (Zeiss, Germany) were set for visualisation of acridine orange fluorescence in lysosomes. The images of red-orange fluorescent cells were acquired using digital videocamera Hamamatsu Orca-ER C4742-95 (Hamamatsu Photonics K.K., Japan), captured and transferred to a IBM-compatible computer P-IV with Firewire data interface card. The fluorescence intensity of randomly selected 100 cell images was measured with AQM Advance 6 software (Kinetic Imaging Ltd., UK) and expressed as an average pixel intensity of gray level for each cell determined CCD.

Six mice were used for each dose treatment. All experiments were repeated in triplicate. The means and standard errors for each treatment were calculated and plotted using SigmaPlot 3.02 software (Jandel Scientific, San Rafael, Calif.).

Frondoside A injected at low subtoxic concentrations in the range of 0.002–2.0 µg/mouse caused significant immunostimulatory effect upon mouse peritoneal macrophages in a dose-dependent manner. The injection of these doses of glycoside resulted in an increase in the number and volume of lysosomes as well as their acidity in mouse peritoneal macrophages, as measured by acridine orange fluorescence. The maximal stimulatory effect was detected at concentration of Frondoside A of 0.2 µg/mouse and it was estimated as more then two fold stimulation of their lysosomal activity. On the other hand, the much bigger doses of 20 µg/mouse and 200 µg/mouse caused the opposite effect expressed as significant lysosomal activity suppression compare to control level. The results are shown on FIG. 1.

Hence, the dose-response relationship of Frondoside A immunomodulatory activity was determined. We report that Frondoside A produces immunostimulatory effect at low subtoxic concentrations and causes inhibitory effects upon macrophage lysosomal activity (hundred-fold and bigger concentrations).

EXAMPLE 5

Lysosomal activity was determined as described in Example 3. Four mice were used for each dose treatment. The means and standard errors for each treatment were calculated and plotted using SigmaPlot 3.02 software (Jandel Scientific, San Rafael, Calif.).

All experiment was carried out during 24 days. The activity of macrophage lysosomes of control animals did not change significantly during all this time. The effect of Frondoside A was evaluated rapidly and significant stimulation was detected even on the $1^{st}$ day after injection. The maximal stimulating effect of Frondoside A was shown on 4–$5^{th}$ days after glycoside injection (FIG. 2). After this period the effect was decreased slowly and reached the control level on the 12–$18^{th}$ day of experiment, and did not change up to $24^{th}$ day of experiment.

Hence, the stimulatory effect of Frondoside A after single injection was observed within two weeks.

EXAMPLE 6

Phagocytosis was observed and quantitated in mouse macrophages by following the internalization of a foreign particle such as fluorescently labeled bacterial particles. This technique takes advantage of the detectability of the intracellular fluorescence emitted by the engulfed particles, as well as the effective fluorescence quenching of the extracellular probe by trypan blue.

Bacteria *S. aureus* (209 strain) were inactivated by heating for 40 min at 100° C. and then incubated at a concentration of $1 \times 10^9$ bacteria/ml with 0.1 mg/mL fluorescein isothiocyanate (FITC "Sigma" dissolved in DMSO,) in 50 mM $NaHCO_3$ in 100 mM NaCl (pH 9.5) for 7 h at +4° C. in the dark. The bacteria were then washed twice with PBS (centrifugation, 1000×g, 25 min) to remove free FITC and resuspended in PBS to a concentration of $1 \times 10^8$ bacteria/mL. The labeled bacteria was kept at –70° C. until experiments.

Phagocytosis was estimated according to the Molecular Probes protocol for the Vybrant™ Phagocytosis Assay Kit.

Macrophages were isolated from BALB/c line mouse peritoneal fluid using standard method. Cell suspension (100 µL) at concentration of $1 \times 10^6$ cell/ml in PBS was transferred to each well of 96-well microplate and 50 µL of Frondoside A solution in PBS at different concentrations was also added. Some negative (without macrophages) and positive (without effector) controls were also included in to the experimental microplate set. Loaded microplates were placed it to the incubator at 37° C. for at least 1 hour to allow the cells to adhere to the microplate surface and for cell incubation with test compound. Then, medium was removed from all of the microplate wells by vacuum aspiration and 100 µL of the prepared FITC-labeled bacteria suspension at concentration of $1 \times 10^7$ bacteria/ml was added to all experimental wells and microplate was transferred in to the incubator for 2 hours. Then, a fluorescent bacteria loading suspension was removed and 100 µL of the prepared trypan blue solution was immediately added to all of the wells (final concentration of trypan blue is 0.25 mg/mL). Microplate was incubated for 1 minute at room temperature and then medium was removed by vacuum aspiration.

After that the fluorescence of the experimental and control wells of the microplate were read in the fluorescence plate reader Fluoroscan Ascent ("ThermoLabsystems", Finland) at 485 nm excitation and 518 nm emission filter pair set. The phagocytosis response to the effector was then expressed as follows:

% Effect=Net Experimental Reading/Net Positive Reading×100% where:

Net Experimental Reading—subtraction of the average fluorescence intensity of a group of negative-control wells from that of a group of identical experimental wells to obtain the Net Experimental Reading. This value represents phagocytosis in response to the effector.

Net Positive Reading—subtraction of the average fluorescence intensity of a group of negative-control wells from that of a group of positive-control wells to yield the Net Positive Reading. This value represents phagocytosis under normal physiological conditions.

Effector concentrations were analyzed in groups of 4–5 replicates. All experiments were repeated in triplicate.

Frondoside A acted as an immunomodulator in dose-depended manner. In the concentration range of 0.01–0.0001 µg/mL, Frondoside A stimulated phagocytosis of bacteria with maximal effect of about 20% at concentration of 0.001

μg/mL (FIG. 3). At a concentration of 1 μg/mL, the glycoside significantly inhibited phagocytosis and at a concentration of 0.1 μg/mL, a non-significant phagocytosis reduction was also observed.

EXAMPLE 7

The oxidative burst in mouse peritoneal macrophages was estimated by the amount of nonfluorescent dihydrorhodamine 123 after its oxidation during the intracellular respiratory burst to rhodamine 123 emiting a bright green fluorescent signal upon excitation by blue light. Conversion of dihydrorhodamine 123 to rhodamine 123 reflects a production of mouse macrophage $H_2O_2$, $O_2$ and peroxynitrite, which is associated with nitric oxide production and NADPH-oxidase dependent superoxide formation.

The fluorescence image analysis was carried out according to methods (with some modifications) to detect respiratory burst in macrophages. (E. W. Childs, K. F. Udobi, J. G. Wood, F. A. Hunter, D. M. Smalley, L. Y. Cheung, "In vivo Visualization of Reactive Oxidants and Leukocyte-Endothelial Adherence Following Hemorrhagic Shock," Shock. 2002.18, 423–7); (S. F. Emmendorffer, M. Hecht, M.-L. Lohman-Mattes, J. Roester, "A Fast Easy Method to Determine the Production of Reactive Oxygene Intermediates by Human and Murine Phagocytes Using Dihydrorodamine 123," J. Immunol. Meth. 1990. 131, 269–275).

For this purpose 250 μL of a BALB/c mice peritoneal fluid was applied on a microscope cover glass and left at 37° C. in an incubator for one hour. After adhesion of macrophages, the cover glasses were washed (3×) with phosphate-buffered saline (PBS, pH 7.5). 250 μL of Frondoside A solution at different concentration in PBS was added to cell monolayer and glasses were incubated additionally 1 h at 37° C. Following incubation, cells were washed (3×) again and 250 μL of dihydrorhodamine 123 solution ("Sigma", 100 ng/mL in PBS including 0.5 mM sodium azide) was added dropwise to the cell monolayer, and glasses were incubated at 37° C. for 10 min. The cell monolayers were then washed (3×) in PBS and cover glasses were mounted on a cell chamber of fluorescent imaging system based on inverted microscope Axiovert 200 (Zeiss, Germany). The 75 W Optosource xenon arc lamp and DAC-controlled Optoscan monochromator (Cairn Research Ltd., UK) was used as a light source to excite fluorescence at $\lambda$=488 nm; HQ FITC filter-block (Chroma Technology Corp., USA) and A-Plan 40×/0.65 Ph2 objective (Zeiss, Germany) were set for visualisation of rhodamine 123 fluorescence in cells. The images of green fluorescent cells were acquired using digital CCD video camera Hamamatsu Orca-ER C4742-95 (Hamamatsu Photonics K. K., Japan), captured and transferred to a IBM-compatible computer P-IV with Firewire data interface card. The fluorescence intensity of randomly selected 300 cell images was measured with AQM Advance 6 software (Kinetic Imaging Ltd., UK) and expressed as an average pixel intensity of gray level for each cell determined.

All experiments were repeated in triplicate. The means and standard errors for each treatment were calculated and plotted using SigmaPlot 3.02 software (Jandel Scientific, San Rafael, Calif.).

Frondoside A caused dual effect upon ROS formation in mouse macrophages. This effect depended on applied glycoside concentration. In a Frondoside A concentration range of 0.0001–0.01 μg/mL, the increase of green intracellular fluorescence of formed rhodamine 123 was detected. The stimulatory effect with maximal efficiency at concentration of 0.001 μg/mL was determined. On the other hand, Frondoside A applied at cytotoxic concentration of 1.0 μg/ml significantly inhibited the ROS generation, and concentration of 0.1 μg/mL was practically ineffective compared to control level (FIG. 4).

EXAMPLE 8

Laboratory albino mice were used in acute toxicity experiments. Each experimental group consisted of 6 animals (19–21 g of weight). Frondoside A in 0.9% NaCl solution at different doses was injected i.p. in volume of 0.5 mL per animal. Physiological solution without Frondoside A was injected as a control. The scheme of glycoside application is shown in Table 1.

TABLE 1

| Scheme of injections. | |
|---|---|
| Groups of animal | Dose, mg/kg |
| $1^{st}$ | 50 |
| $2^{nd}$ | 25 |
| $3^{rd}$ | 12.5 |
| $4^{th}$ | 6.25 |
| $5^{th}$ | 3.125 |
| $6^{th}$ | 0 (control) |

Observation for animals was carried out during two weeks, the number of dead and live animals was determined daily.

The Karber method (G. Karber, Arch. Exp. Pathol. Pharm. 1931, 162, 480.) was applied to estimate $LD_{50}$ using following formula:

$LD_{50}=LD_{100}-\Sigma(zd)/m;$ where:

$LD_{100}$—dose which caused effect in all animals in group;

z—average arithmetic (mean) number of animals where effect was seen under influence of two adjacent doses;

d—interval between each two adjacent doses;

m—number of animals in each group.

The acute intraperitoneal toxicity ($LD_{50}$) for Frondoside A was estimated as 9.9 mg/kg

EXAMPLE 9

Erythrocytes were isolated from mouse blood, washed three times with PBS (pH 7.4) using centrifugation (450×g, 10 min), and the residue of erythrocytes was resuspended in PBS to a final concentration of 1.0% and kept on ice.

For the hemolytic assay, 100 μL of Frondoside A water solution at different concentrations were mixed with 900 μL of erythrocyte suspension and incubated at 37° C. for 1 h. The residual cells were sedimented by centrifugation, aliquots of supernatant (200 μL) were transferred to the wells of 96-well microplates and the hemoglobin concentration in the supernatant was evaluated spectroscopically at $\lambda_{ex}$=541 nm with "μQuant" plate reader (Bio-Tek Instruments, Inc). The results were expressed as percent of hemolysis and plotted.

Frondoside A caused hemolytic effects upon mouse erythrocytes. Effective concentrations of hemolysis were 3.5 μg/mL ($EC_{50}$) and 12.50 μg/mL ($EC_{100}$).

EXAMPLE 10

The sea urchin *Strongylocentrotus nudus* embryos were used as a test material for embryotoxicity bioassays, according to the method of Kobayashi with some modifications. To isolate the mature eggs or sperm, 1–2 mL of 0.5M KCl solution was injected into the cavity of a sea urchin. The eggs and sperm (separately) were collected into glass beakers with sea water. When the female had completely spawned, the eggs were allowed to settle to the bottom of the cultivator box filled with filtered and aspirated sea water and then sea water. This process was repeated 3 times in order to wash out the egg's jelly coating. After artificial fertilization, 0.9 ml of egg suspension with density of $1 \times 10^3$ cell/mL was put into each well of a 24-well microplate containing the sample solutions (0.1 mL) and the plate was kept at 20–22° C. during 2 h before stage of 8-blastomeres (control). Then aliquots of formaldehyde solution (2%) were added to each well to fix the embryos. A hundred embryos were examined at each concentration of toxicant and the number of developed 8-blastomeres were determined with the inverted microscope. All experiments were repeated in triplicate. The results were expressed as percent of the controls and plotted.

The means and standard errors for each treatment were calculated and effective concentrations were estimated from dose-response plots using SigmaPlot 3.02 software (Jandel Scientific, San Rafael, Calif.).

Frondoside A causes embryotoxic effects upon sea urchin developed embryos, correspondingly. Effective concentrations of the embryotoxicity were 0.98 μg/mL ($EC_{50}$) and 3.12 μg/mL ($EC_{100}$).

EXAMPLE 11

ISCOM Preparation

General Experimental Approach

ISCOMs are prepared from a base of Frondoside A, cholesterol, egg phosphatidylcholine and antigen of influenza virus in a molar ratio of 1:1:1:1. Preparation method #1: the latter 3 components (cholesterol, egg phosphatidylcholine and antigen of influenza virus) are placed on top of a 10–40% sucrose gradient containing 0.1% pure Frondoside A and a neutral, low ionic strength buffer, for example PBS. The tube is ultra-centrifuged for 4 hours at 150000 g, and ISCOMs form at 19S near the middle of the gradient. These are subsequently washed by re-centrifugation through 20% sucrose.

Preparation method #2: if detergents with high critical micelle concentrations are used for antigen preparation (eg. when isolating viral envelope proteins), then the dialysis method for ISCOM preparation is applied. In this procedure, the cholesterol, egg phosphatidylcholine and antigen of influenza virus are mixed with Frondoside A to give a final glycoside concentration of 0.1%. Following 24 hour dialysis to remove the detergent, ISCOMs are form and excess glycoside is removed by 20% sucrose ultra-centrifugation at 4 hours at 150000 g. [Pete, I have deleted the phrase concerning other sea cucumber because of the situation with *C. japonica* you know]

In any ISCOMs type the concentration of Frondoside A should be 100 μg per ml of ISCOM suspension. FW's of ISCOM components are: cholesterol—386.7 Da, egg phosphatidylcholine—aprox 700 Da, nonstructural protein of influenza A virus—26 kDa. Therefore, the 1 ml of all ISCOM components should consist of: cholesterol—386.7 mg, egg phosphatidylcholine—700 mg, nonstructural protein of influenza A virus—26 g. This 1 ml of composition is mixed with 100 μg of Frondoside A to give final glycoside concentration of 100 μg/ml or 0.01%.

Immune Potentiation in Stressed Animals and Humans

EXAMPLE 12

Determining Increase of Immune Surveillance in Baby Swine Experimental Design Two groups of 10 of 11 day-old weaned pigs are isolated from the other group, and entered into a trial designed to determine the efficacy of Frondoside A as an subcutaneously injected immune stimulating agent capable of protecting farm raised swine from opportunistic diseases associated with decreased immune response common in such conditions. Group A pigs are injected with Frondoside A subcutaneously at a dose 1 microgram per kilogram body weight every ten days for four months. Group B has no intervention. At the end of four months, those pigs in Group A so injected are determined to have lower mortality and incidence of disease rates than Group B, the un-treated group by a significant difference.

Susceptibility to infectious diseases at weaning may be attributed to several factors, including loss of maternally derived antibodies, developmental deficiencies in the immune response, and elevated glucocorticoid levels in animals during weaning. Production pressures on the swine industry force producers to look for ways to increase production. One possible means to attain increased production would be to wean piglets from sows earlier. However, weaning pigs and other species at an early age has been shown to have deleterious effects on the health and survivability of these animals, most likely due to a deficient immune response and subsequent inability to fight off infections [Blecha et al., 1983, (ibid); Wilcock and Schwartz (ibid); El-Awar and Hahn (ibid); Carter and Martens (ibid); Drieson et al. (ibid); Selim et al. (ibid); Shi et al., J. Leuk. Biol. 1994, 56, 88–94; and Hoskinson et al., J. Anim. Sci. 1990, 68, 2471–2478]. If loss of maternal antibodies and developmental deficiencies in the immune response of young pigs are at least partially responsible for the increased susceptibility to bacterial disease observed at weaning, early weaning of pigs leaves these animals at an even greater defensive disadvantage, immunologically speaking, than pigs weaned at older ages.

EXAMPLE 13

Determination of Anti-Aleutian Disease Virus Activity in Mink and Ferrets. Experimental Design:

Aleutian Disease in mink and ferrets is a parvo virus with no current effective therapy. Disease progression includes immune complex deposition in various organs, IL-6 expression, neurological pathology, musculosketal auto-immune like symptoms, inflammatory conditions, wasteing, ultimate decline and in a certain percentage of affected animals, immune exhaustion and death.

In an Aleutian Disease hospice environment for pet ferrets, Frondoside A is administered at 1 microgram per kilogram body weight subcutaneously in 10 Aleutian Disease infected ferrets with compromised immune systems exhausted by the disease. At the end of three months, disease activity is decreased as determined by anti-body determination compared to starting levels in each individual. Symptoms of immuno-competence and symptomology improve.

EXAMPLE 14

Frondoside A and Antiprotozoal Drug Treatment of *Pneumocystis carinii* Infection Associated with HIV in Humans. Experimental Design:

A HIV-1 study patient is admitted to a hospital for *Pneumocystis carinii* pneumonia (PCP). The patient responds to 2 weeks of aerosolized pentamidine and Frondoside A therapy, with doses of Frondoside A at 1 microgram per kilogram body weight administered IP. He becomes symptom free after two weeks.

EXAMPLE 15

Determination of Increase in CD-4 Counts in HIV Infected Humans. Experimental Design:

It is expected that the immune potentiating activity shown above in in vitro and in vivo experiments will have application to HIV pathology in humans. As an illustrative example, 20 HIV positive individuals with CD-4 counts below 250 are dosed every week IM with Frondoside A in physiological solution at 3 micrograms per kilogram body weight. After 4 months of such treatment, CD-4 counts rise to normal levels of higher than 400, opportunistic disease pathology decreases and the individuals become increasingly free of symptoms of the disease. Increased macrophage phagocytosis, with anti-viral activity is determined to be responsible for the observed effects.

EXAMPLE 16

Determination of Resistance to Anthrax Bacteria in Humans

Experimental Design:

Since increased immune surveillance in a mammal is a factor in protection against bacterial infection, humans being administered Frondoside A of the present invention are determined to have more resistance against a bio-terror assault involving anthrax or weaponized anthrax. In an anticipated experiment, laboratory animals are divided into two groups, Group A and Group B. Group A and B are infected with anthrax in methods known to those persons skilled in the arts. Only Group A is treated 10 days prior to and for the two month course of the study, with Frondoside A dosed intraperitoneally at a rate of 3 micrograms per kilogram body weight. It is determined that Group A is protected in a significant manner, with 60% more animals alive at experiment end. It can be extrapolated that such an animal experiment, or one conducted within the teachings of this invention, will be clinically relevant to a human population, such as soldiers at risk of infection by anthrax or other bacterial pathogens.

It is understood that the foregoing detailed description is given merely by way of illustration and that modifications and variations may be made therein without departing from the spirit and scope of the invention.

EXAMPLE 17

ISCOM Testing

General Experimental Approach

ISCOM's containing influenza antigen, Frondoside A, cholesterol and phosphotidylcholine as previously described are administered orally over the course of 14 days to 10 patients experimentally infected with the influenza virus. Ten additional volunteers are infected experimentally, but receive no ISCOM's or other means of treatment. ISCOM treated patients receive oral administration of 1 milliliter of Frondoside A ISCOM's once per day during the trial. At the end of 14 days, the placebo group of patients are determined to have more influenza virus symptoms than the ISCOM-treated group. Additional routes of delivery including intranasal are utilized in further studies of placebo and ISCOM treated groups, with similar results indicating that Frondoside A incorporating ISCOM formulations are effective by intranasal route.

EXAMPLE 18

ISCOM Testing

General Expeimental Approach:

ISCOM's (ISCOM-MATRIX) containing Frondoside A, cholesterol and phosphatidylcholine as previously described, but without antigen are administered orally to pet ferrets in need of immune stimulation resulting from immune depression from Aleutian Disease of long duration. ISCOM's providing approximately 10 micrograms orally of Frondoside A in a 1:1:1 Frondoside A:cholesterol:phospholipid ISCOM are administered by oral lavage once per day for 14 days. At the end of 14 days, observed sympotomology of Aleutian Disease is considered to be improved by owners of the animals.

The daily dosage of Frondoside A included into any types of ISCOM should be 1 μg per kg of patient body weight. Therefore, 1 ml of ISCOM solution should include 100 μg of Frondoside A as described previously in Example 11. If patient will be treated with 1 ml of ISCOM solution a day, then the overage dosage of Frondoside A for patient with overage weight of 100 kg will be 1 μg/kg a day.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A method for recovering *Cucumaria frondosa* saponins which comprises:
   i) extracting (a) freeze dried form of water which had been used to cook *Cucumaria frondosa* in the industrial processing of *Cucumaria frondosa*, wherein said water contains *Cucumaria frondosa* residues, or (b) dried and powdered tissues of *Cucumaria frondosa* with a mixture of chloroform and methanol under reflux to obtain an organic extract;

ii) evaporating the extract;

iii) extracting the evaporated extract with ethyl acetate and water one or more times to obtain an aqueous phase;

iv) combining the aqueous phase from each ethyl acetate and water extraction;

v) performing chromatography of the aqueous phase on Teflon or other non-polar resin and Silica gel columns; and vi) collecting the eluate to obtain *Cucumaria frondosa* saponins.

2. The method of claim 1 wherein the extracting with chloroform and methanol mixture is carried out using solvents in a proportional ratio of approximately 4 mL of said solvent mixture to 1 g of said freeze dried form of water.

3. The method of claim 1 wherein the extracting with chloroform and methanol mixture is carried out using solvents in a proportional ratio of approximately 6 mL of said solvent mixture to 1 g of said freeze dried form of water.

4. A method for recovering and assaying orally bioavailable *Cucumaria frondosa* saponins comprising:

i) extracting (a) freeze dried form of water which had been used to cook *Cucumaria frondosa* in the industrial processing of *Cucumaria frondosa*, wherein said water contains *Cucumaria frondosa* residues, or (b) dried and powdered tissues of *Cucumaria frondosa* with a mixture of chloroform and methanol under reflux to obtain an organic extract;

ii) evaporating the extract;

iii) extracting the evaporated extract with ethyl acetate and water one or more times to obtain an aqueous phase;

iv) combining the aqueous phase from each ethyl acetate and water extraction;

v) performing chromatography of the aqueous phase on Teflon or other non-polar resin and Silica gel columns;

vi) collecting fixed-volume fractions of the aqueous phase after chromatography, and evaporating and redissolving said fixed-volume fractions in water; and vii) assaying each redissolved fraction for oral bioavailability by administering oral doses of redissolved fractions to a test animal, monitoring metabolites, and comparing results to placebo fractions.

* * * * *